United States Patent [19]

Wiesmann

[11] Patent Number: 4,751,392
[45] Date of Patent: Jun. 14, 1988

[54] APPARATUS FOR STERILIZING LIQUIDS

[75] Inventor: Rudolf Wiesmann, Gossau, Switzerland

[73] Assignee: BBC Brown, Boveri & Company, Limited, Baden, Switzerland

[21] Appl. No.: 9,787

[22] Filed: Feb. 2, 1987

[30] Foreign Application Priority Data

Feb. 12, 1986 [CH] Switzerland .................... 556/86

[51] Int. Cl.⁴ ........................................... G01N 21/01
[52] U.S. Cl. .................................. 250/429; 250/436; 422/24
[58] Field of Search .............. 250/429, 435, 436, 437, 250/438; 422/24, 109

[56] References Cited

U.S. PATENT DOCUMENTS

| | | | |
|---|---|---|---|
| 3,637,342 | 1/1972 | Veloz | 250/436 |
| 4,179,616 | 12/1979 | Coviello | 250/429 |
| 4,250,391 | 2/1981 | Bearda | 250/436 |
| 4,323,810 | 4/1982 | Horstmann | 250/436 |
| 4,336,456 | 6/1982 | Kuse et al. | 250/436 |
| 4,576,792 | 3/1986 | Martensson | 422/109 |

FOREIGN PATENT DOCUMENTS

| | | |
|---|---|---|
| 631283 | 12/1927 | France . |
| 2177012 | 11/1973 | France . |
| 2452289 | 10/1980 | France . |
| 636479 | 5/1983 | Switzerland . |
| 651272 | 3/1951 | United Kingdom . |

Primary Examiner—Bruce C. Anderson
Attorney, Agent, or Firm—Oblon, Fisher, Spivak, McClelland & Maier

[57] ABSTRACT

In the apparatus, a low-pressure high-current mercury-vapor lamp (4) equipped with a tubular extension (6) arranged on the discharge tube is used as a radiation source. So that the temperatures of the tubular extension (6) can be regulated specifically even during the operation of the ultraviolet lamp (4), and to achieve a longer service life of the ultraviolet lamps, and airstream circulating through the apparatus and serving at the same time for heating the tubular extension (6) is used to cool the ultraviolet lamp (4). A metal heat-conducting body (25) surrounding the tubular extension (6) and having a temperature sensor (28) regulates the temperature of the tubular extension (6) to a predetermined value in conjunction with a cooling device (18) and a guide device (22). There is therefore no need for separate heating of the extension. Furthermore, the heat-conducting body (25) acts as a thermal and electrical shield for the temperature-measuring circuit.

11 Claims, 3 Drawing Sheets

APPARATUS FOR STERILIZING LIQUIDS

FIELD OF THE INVENTION

The invention relates to an apparatus for sterilizing liquids by means of ultraviolet rays, with a low-pressure high-current mercury-vapor lamp as a radiation source.

BACKGROUND OF THE INVENTION

The invention is an improvement over the state of the art represented for example, by Swiss Patent Specification No. 631,950. Apparatuses of this type are used increasingly for sterilizing industrial, drinking or swimming-pool water, or also beverages, essences, concentrates or oils, provided that the last-mentioned liquids have sufficient permeability to the ultraviolet rays (that is to say, ultraviolet rays can pass through them). Because the discharge tube of the ultraviolet lamp possessed a tubular extension for adjusting the mercury vapor pressure, in the apparatuses used hitherto the space in which the ultraviolet lamp was fastened was essentially divided into three chambers separated from one another in thermal terms: a bottom chamber in which the tubular extension of the ultraviolet lamp was located, a middle chamber in which there was the discharge space of the lamp and round which flowed the liquid to be sterilized, and an upper part in which the electrode bulbs were accommodated and which was cooled by cooling fins. The three-chamber division therefore appeared to be necessary in order to ensure, on the one hand, that the operating temperature of the discharge zone (as a rule, $\geq 300°$ C.) did not overheat the tubular extension which, as the coldest point of the system (as a rule, $\leq 65°$ C.), is responsible for the mercury vapor pressure and consequently also for the radiation intensity, and, on the other hand, that the upper space was also not overheated by the discharge zone, because this space accessible from outside was not allowed to become too hot for safety reasons.

So that the ultraviolet lamp could be ignited at all, the entire portion round the tubular extension had to be preheated via a heating resistor before ignition. This heating was then cut out again when the anode current was switched on. During operation, the temperature of the tubular extension was determined by the backheating of the discharge zone and the temperature of the ambient air. This in turn fluctuated with the water temperature. Depending on the season, the temperature of the tubular extension therefore had to be corrected by suitable intermediate rings, by means of which the tubular extension was embedded to a greater or lesser extent in the bottom chamber.

The disadvantage of the previous apparatuses was that, when the tubular extension was heated to ignition, the middle part, and consequently the discharge zone, remained cold. The mercury was therefore able to condense again there, thus making ignition more difficult. On the other hand, during operation, the high temperature of the discharge zone in the middle chamber had an extremely detrimental effect on the service life of the ultraviolet lamp.

In Swiss Patent Specification No. 631,950 mentioned in the introduction, a low-pressure high-current mercury-vapor lamp equipped with a tubular extension arranged on the discharge tube is used as a radiation source. So that the temperature of the tubular extension can be regulated specifically even during the operation of the ultraviolet lamp, and to ensure a longer service life of the ultraviolet lamp, an airstream circulating through the apparatus is used to cool the ultraviolet lamp. This airstream is guided in such a way that the air heated at the discharge tube flows past the electrode bulbs of the ultraviolet lamp and into a connecting pipe to the outer wall of the line pipe, through which the liquid to be sterilized flows. The air cooled on the outer wall of the line pipe is then delivered to the ultraviolet lamp once again and must have a temperature which is less than the operating temperature of the tubular extension. The setting of the predetermined temperature is regulated via the sensor by means of a heater.

To reduce the power consumption for heating the tubular extension, Swiss Patent Specification No. 636,479 proproposes to divide the cooling stream into two parts:

One part stream is conveyed directly to the discharge tube of the ultraviolet lamp; the other part stream, which is smaller in comparison with the first, is heated by the heater and delivered to the tubular extension.

Apparatuses according to the Swiss Patent Specifications mentioned have proved outstanding in the past in many uses and have made a substantial contribution to the operating reliability and to a longer service life and therefore greater availability of the installations equipped with these lamps.

OBJECT OF THE INVENTION

The object of the invention is based is to perfect the known apparatus for sterilizing a liquid in terms of its total power consumption and at the same time to modify it for installations using a large number of ultraviolet rays such as are required, for example, in the sewage industry or in off-shore technology.

SUMMARY OF THE INVENTION

The essential feature of the invention is that it does away with separate heating devices and the associated individual regulating arrangements for keeping the temperature of the tubular extension constant. Instead of cooling the entire cooling-air stream or even only a part stream down to temperature values below the optimum operating temperature of the tubular extension and subsequently reheating it, the invention utilizes in a logical way the heat loss of the ultraviolet lamp itself both in the starting phase and in regular operation.

How this is particularly put into practice and the advantages arising from the new cooling concept are explained in detail below with reference to exemplary embodiments illustrated in the drawings.

DETAILED DESCRIPTION OF THE PRESENTLY PREFERRED EMBODIMENTS

Figure 1:
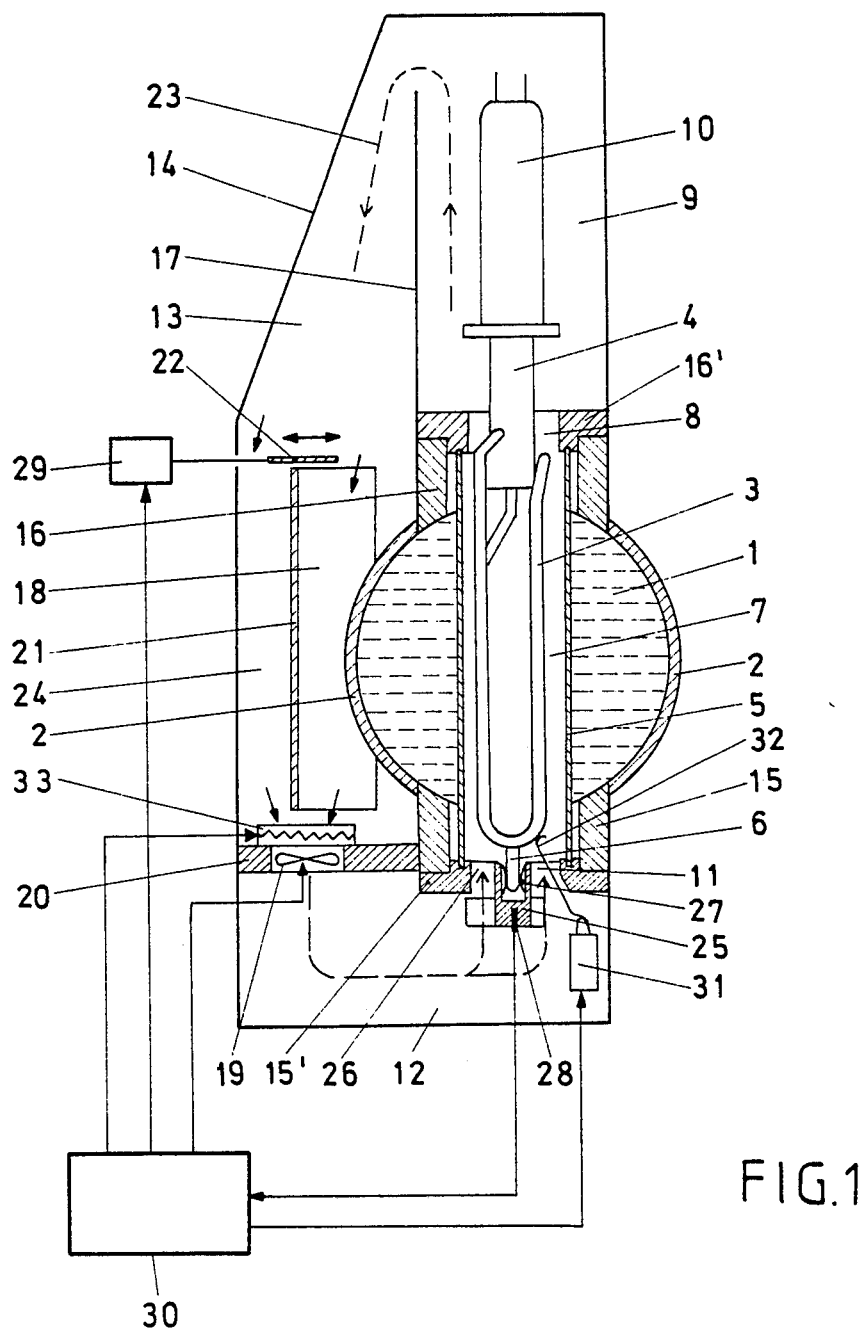
FIG. 1 shows, in cross-section, a first embodiment of a sterilizing apparatus with internal cooling.

In FIG. 1, the medium to be sterilized 1 flows through a line pipe 2, in which a, for example, U-shaped discharge tube 3 of an ultraviolet lamp 4 is arranged in a quartz guard tube 5. At the bottom end of the discharge tube 3 there is a tubular extension 6. A first air-filled space 7 surrounding the discharge tube 3 has an orifice 8 to a second air-filled space 9 which is located above it and which surrounds an electrode bulb 10 of the ultraviolet lamp 4. The first air-filled space 7 communicates via an orifice 11 with a third air-filled space 12.

The second and third air-filled spaces 9 and 12 communicate with one another via a connecting duct 13. The connecting duct 13 is formed by one half of a housing 14 surrounding the ultraviolet lamp 4, by the line pipe 2, together with supporting parts 15, 16, projecting into the connecting duct 13, and by a partition wall 17 extending up to the top end of the electrode bulb 10. Cooling plates 18 projecting into the connecting duct 13 are fastened to the line pipe 2.

Arranged directly below the cooling plates 18 is a fan 19 which is fastened in a bulkhead 20. Thus, the third air-filled space 12 communicates with the connecting duct 13 via the fan 19 cross-section only.

The cooling plates 18 are covered, at the end facing the housing 14, with a partition wall 21 located at a distance from the housing 14. A slide 22 is movable back and forth by a drive 29 in the direction indicated by a two-headed arrow. The slide 22 makes it possible to direct an air flow 23, indicated by arrows, in the connecting duct 13 on the one hand only through the gaps between the cooling plates 18 or only through a circulation duct 24 formed between the partition wall 21 and the housing 14, whilst in the intermediate position of the slide 22 the air can follow both flowpaths to a greater or lesser extent.

The tubular extension 6 penetrates over the predominant part of its length into the inner spaces of a pot-shaped metal heat-exchange body 25, hereafter called a thermal block. The thermal block 25 is fastened to the bottom end of the quartz guard tube 5 by means of spoke-like holding arms 26 which can be made in one piece with the thermal block 25 and which improve the heat transfer between the environment and the thermal block 25. The outside diameter of the thermal block 25 is less than the clear width of the quartz guard tube 5, so that the thermal block 25 does not appreciably restrict the flow cross-section of the cooling air through the quartz guard tube 5. The inside diameter of the thermal block 25 is greater than the outside diameter of the tubular extension 6. The remaining annular gap can additionally be provided with a heat bridge which, for example, takes the form of a contact spring 27, in order to improve the heat transfer from the thermal block 25 to the tubular extension 6.

Arranged in an axial bore in the underside of the thermal block 25 is a temperature sensor 28 which, like the drive 29 of the slide 22 and the fan 19, is connected operatively to a control and regulating device 30.

For the sake of completeness, FIG. 1 also shows a high-voltage ignition device 31 having an ignition electrode 32.

When the apparatus is in operation, a distinction must be made between two phases, namely the starting phase (with the ultraviolet lamp cold) and the regular operating phase.

Before the ultraviolet lamp may be ignited, the cathode (in the electrode bulb 10) first has to be heated. The waste heat from the cathode (typically 40–60 W per ultraviolet lamp) heats up the air in the second air-filled space 9. When the fan 19 is switched on and at the same time the slide 22 is moved into the right-hand end position, air circulation is established in the housing 14 from the second air-filled space 9 via the connecting duct 13, through the circulation duct 24 and the third air-filled space 12 into the first air-filled space 7 and back to the second air-filled space 9 containing the "heat source" in the form of the electrode bulb 10. Because there are no "cooling surfaces", apart from the walls of the housing 14, in the course of this flowpath, the entire interior of the housing 14 and (this being of essential importance) also the U-shaped discharge tube 3 together with the tubular extension 6 are heated. When the temperature of the circulated air reaches the ideal value for the ignition of the ultraviolet lamp 4, typically 60° C., the ultraviolet lamp 4 is ignited.

As a result of the close thermal coupling of the tubular extension 6 via the thermal block 25 with the temperature sensor 28, the tubular extension 6 is also at this temperature.

In the regular operating phase which now follows, the ultraviolet lamp 4 heats the air flowing through the first air-filled space 7, its efficiency being only around 30% for physical reasons. This air flows back to the thermal block 25 along the path described above. When the temperature exceeds an adjustable value, in the particular example 60° C., by means of the control and regulating device 30 the conveying capacity of the fan 19 is increased and/or the slide 22 is moved to the left, thereby opening the path through the cooler (cooling plates 18 in conjunction with the heat-exchange medium 1). The number of cooling plates 18 and their size and the dimensions of the surface of the line pipe 2 coming in contact with the air to be cooled are selected in such a way that, even when the ultraviolet lamp 4 is under full load, the temperature of the air at the thermal block 25 does not exceed the predetermined value.

Should it be necessary, as a result of circumstances, for the heating of the cooling air in the starting phase solely by means of the waste heat from the cathode to last too long or the waste heat to be insufficient, an additional heater 33 which can only be cut in in the starting phase and which is otherwise unregulated can be provided in the connecting duct 13, for example directly in front of the fan 19 on the bulkhead 20. However, the additional heater 33 is switched off again immediately before the ignition of the ultraviolet lamp 4—or possibly even previously.

The system described guarantees that the desired temperature responsible for the mercury vapor pressure and consequently also for the radiation intensity is maintained at the tubular extension 6, even under varying operating (temperature) conditions. Above all, to improve the radiator cooling without an additional power consumption, the flow of cooling air can be increased by a multiple, without involving the danger that the temperature of the radiator at the cooling-air inlet will fall below the desired temperature of the tubular extension 6.

Contrary to the arrangement according to Swiss Pat. No. 636,479, this increase in the throughput of cooling air also does not involve the danger that this airstream cooled to below the desired temperature of the tubular extension 6 will overcool the lower portion of the discharge tube 3 adjoining the extension, which can lead to the damage (or even the destruction) of the ultraviolet lamp, especially in the starting phase.

A further advantage of the invention is to be seen in the fact that the thermal block 25 shields the tubular extension 6 thermally from the discharge tube 3, and therefore the radiant heat of the discharge does not heat up the tubular extension 6. At the same time, however, the thermal block 25 also acts as a heat buffer, so that a brief fall of the cooling-air temperature has no direct effect on the temperature of the tubular extension 6. In electrical and magnetic terms also, the thermal block 25 performs a shielding function relative to the temperature sensor 28, because it keeps electrical and magnetic fields, which originate from the discharge and which themselves can have a disturbing effect on the temperature control, away from the temperature sensor 28.

Figure 2:
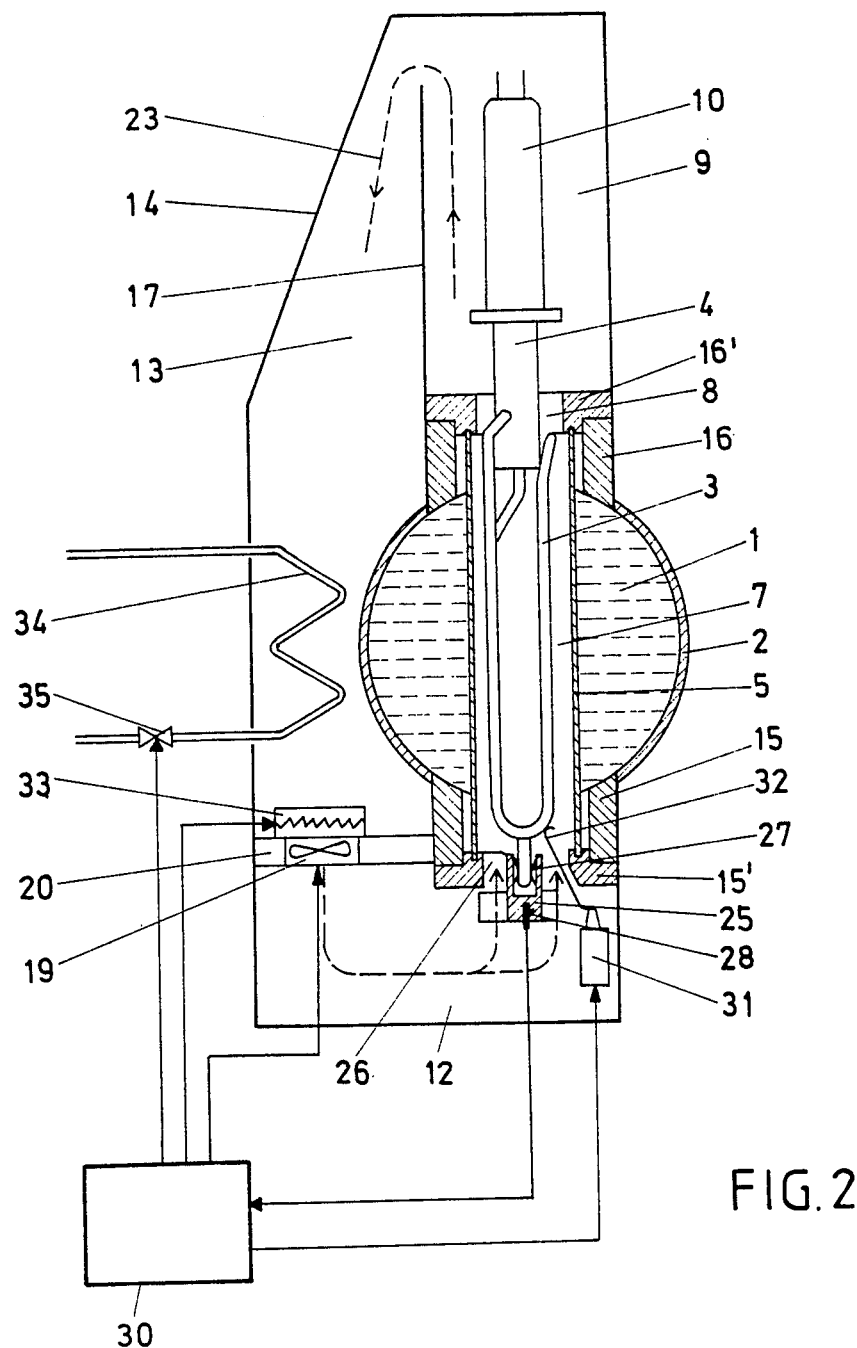
FIG. 2 shows a second embodiment with external cooling.

As illustrated by way of example in FIG. 2, in which the same parts as in FIG. 1 bear the same reference symbols, the invention can also be put into effect with extraneous or external cooling. The cooling plates 18, the partition wall 21 (and consequently the circulation duct 24), and the slide 22 are omitted. These parts are replaced by a cooler 34 which is located in the connecting duct 13 and which can be cut in via a valve 35 connected operatively to the control and regulating device 30.

The mode of operation of the apparatus according to FIG. 2 corresponds basically to that according to FIG. 1. The cooler 34 and/or the fan 19 are cut in and out or controlled as a function of the temperature detected on the thermal block 25.

Figure 3:
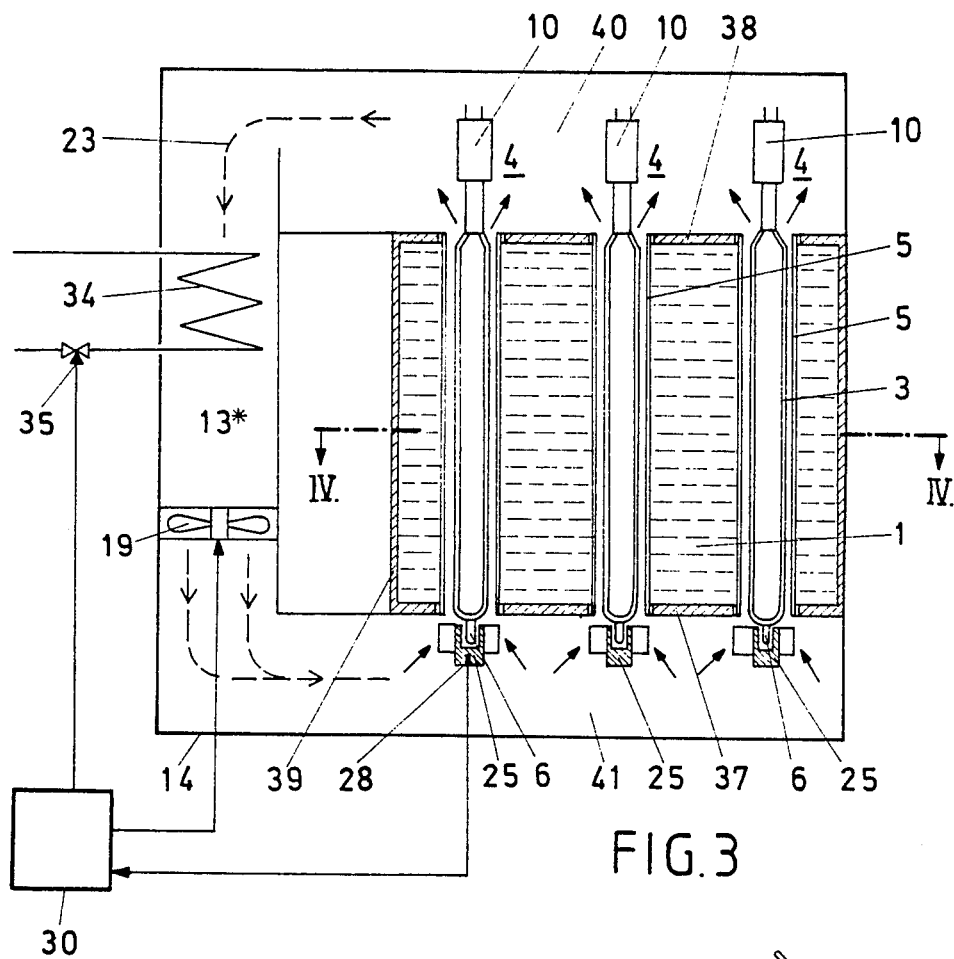
FIG. 3 is a cross-section through a sterilization installation with a plurality of ultraviolet lamps.
Figure 4:
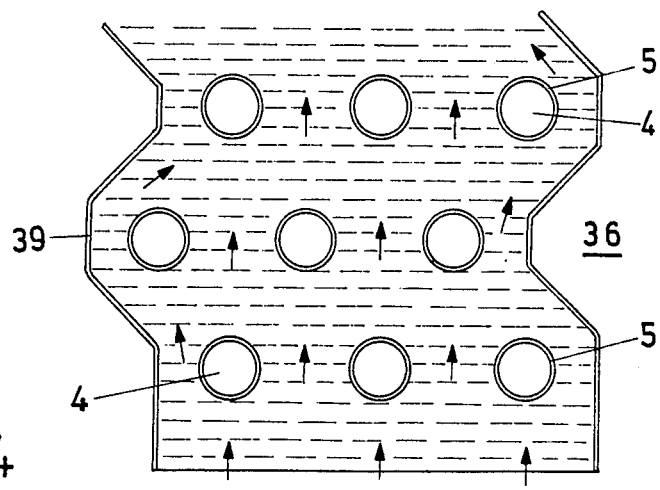
FIG. 4 is a horizontal section through the installation according to FIG. 3 along the line IV—IV.

In comparison with the two known apparatuses (Swiss Patent Specification Nos. 631,950 and 636,479), in which each ultraviolet lamp has to be assigned its own temperature control, in the design according to FIG. 2 it is also possible to provide a common cooler for several ultraviolet lamps, having a common temperature control and with only one temperature sensor 28 on a single thermal block 25. This is illustrated by way of example in simplified form in FIGS. 3 and 4.

The ultraviolet lamps 4 are arranged successively in rows and offset relative to one another in a channel 36 of rectangular cross-section. The channel 36 is limited by bottom plates 37, cover plates 38, and side walls 39. The quartz guard tubes 5 are inserted in a liquid-tight manner in bores of corresponding design in the bottom and cover plates 37, 38. The side walls 39 parallel to the lamp axes are corrugated (FIG. 4) in such a way that the flow cross-section for the medium to be sterilized 1 is approximately the same everywhere and, as a result of thorough mixing, a uniform irradiation of the entire stream of liquid can be obtained. The electrode bulbs 10 of the ultraviolet lamps 4 project at the top into an outflow space 40 which is limited by the cover plates 38 and the upper wall of the housing 14.

The tubular extensions 6 of the discharge tubes 3 are surrounded by the thermal blocks 25 in a similar way to FIGS. 1 and 2 and project into an inflow space 41 which is limited by the bottom plate 37 and the lower wall of the housing 14. The outflow space 40 and inflow space 41 are connected via a duct 13* which is limited by the lateral wall of the housing and the side wall 39. The cooler 34 and the fan 19 are arranged in this duct 13* in a similar way to FIG. 2.

A temperature sensor 28 connected operatively to the control and regulating device 30 is arranged on only one thermal block 25. The mode of operation of the apparatus corresponds to that according to FIG. 2.

Comprehensive measurements have shown that the mixing of the cooling air in the inflow space 41 is so complete that practically the same temperature prevails at all the thermal blocks 25 and consequently at all the tubular extensions 6.

Even in the starting phase, the comparatively dense accumulation of heat sources in the form of the electrode bulbs 10 in the outflow space 40 leads to rapid heating of the cooling air, so that an additional heater can be omitted, if appropriate.

I claim:

1. An apparatus for sterilizing liquids by means of ultraviolet rays, said apparatus comprising a low-pressure high-current mercury-vapor lamp (4) which has a discharge tube (3), a tubular extension (6) arranged on said discharge tube (3), and an electrode bulb (10) located at a distance from said tubular extension (6) and containing a cathode heating system, a first space (7) surrounding said discharge tube (3), said discharge tube being surrounded by a treatment space (2) intended for the liquid (1) to be sterilized, said first space (7) having a first orifice (8) to a second space (9) surrounding said electrode bulb (10) and, at said tubular extension (6), a second orifice (11) to a third space (12), said second space (9), and said third space (12) communicating with one another via a connecting duct (13) containing a cooling device having a cooling surface (18; 34) and a fan (19), said tubular extension (6) being surrounded at least partially by a heat-conducting body (25) which projects at least partially into said third space (12), a temperature sensor (28) being arranged on said heat-conducting body (25) connected operatively to a control and regulating device (30), and there also being, in said control and regularing device (30), means (22; 35) for controlling the throughput of cooling medium through said cooling device, in order to regulate the temperature of said heat-conducting body (25) to a predetermined temperature.

2. An apparatus as claimed in claim 1, wherein said heat-conducting body (25) is made pot-shaped, the free end of said tubular extension (6) penetrating at least partially into the interior of said heat-conducting body (25).

3. An apparatus as claimed in claim 2, wherein a heat bridge (27) is provided between the inner wall of said heat-conducting body (25) and said tubular extension (6).

4. An apparatus as claimed in claim 1, wherein said cooling device comprises cooling plates (18) projecting into said connecting duct (13), said cooling plates (18) being covered laterally by means of a partition wall (21) in such a way that a circulation duct (24) is formed between said partition wall (21) and a wall of a housing (14) containing said duct (13), and wherein said means for controlling the throughput of cooling medium comprises means for selectively closing said circulation duct (24) and opening a flowpath through the gaps between said cooling plates (18) as a function of the temperature of said heat-conducting body (25).

5. An apparatus as claimed in claim 1, wherein a cooler (34) and means (35) for controlling the cooling capacity of said cooler (34) as a function of the temperature of said heat-conducting body (25) are provided in said connecting duct (13).

6. An apparatus as claimed in claim 1, wherein a heat source (33) which can be cut in only in the starting phase is provided in said connecting duct (13).

7. An apparatus as claimed in claim 1, wherein a plurality of ultraviolet lamps (4) as recited in claim 1 are arranged in a common housing (14), a plurality of the ultraviolet lamps (4) having assigned to them a common cooling device (34) the cooling capacity of which can be controlled by a single temperature sensor (28) via said control and regulating device (30).

8. An apparatus as claimed in claim 7, wherein said common housing comprises a treatment space for the liquid to be sterilized, an inflow space (41), an outflow space (40) for the cooling medium, and a duct (13*) connecting the two last-mentioned spaces, said electrode bulbs (10) projecting into said outflow space (40) and said tubular extensions (6) surrounded by said heat-conducting bodies (25) projecting into said inflow space (41).

9. An apparatus as claimed in claim 8, wherein said treatment space is limited by bottom plates (37), cover plates (38), and side walls (39), the bottom and cover plates (37, 38) having congruent bores, in which quartz guard tubes (5) of said plurality of ultraviolet lamps (4) are fastened in a liquid-tight manner.

10. An apparatus as claimed in claim 9, wherein the individual ultraviolet lamps (4) are arranged successively in rows and offset relative to one another, and said side walls (39) are corrugated.

11. An apparatus as claimed in claim 1, wherein said heat-conducting body (25) is made out of metal.

* * * * *